United States Patent
Sikora et al.

(10) Patent No.: US 8,105,065 B2
(45) Date of Patent: Jan. 31, 2012

(54) APPARATUS FOR THE MEASUREMENT OF THE TEMPERATURE OF A PLASTIFIED PLASTIC MATERIAL AT THE EXIT OF AN EXTRUDER

(75) Inventors: Harald Sikora, Bremen (DE); Torben Clausen, Weyhe (DE)

(73) Assignee: Sikora AG, Bremen (DE)

( * ) Notice: Subject to any disclaimer, the term of this patent is extended or adjusted under 35 U.S.C. 154(b) by 11 days.

(21) Appl. No.: 12/577,371

(22) Filed: Oct. 12, 2009

(65) Prior Publication Data

US 2010/0096767 A1  Apr. 22, 2010

(30) Foreign Application Priority Data

Oct. 22, 2008 (DE) .......................... 10 2008 052 740
Jan. 9, 2009 (DE) .......................... 10 2009 004 946

(51) Int. Cl.
*B29C 45/77* (2006.01)
*B29C 45/78* (2006.01)

(52) U.S. Cl. ......... 425/143; 425/144; 425/145; 425/170
(58) Field of Classification Search .................. 425/170, 425/143, 144, 145
See application file for complete search history.

(56) References Cited

U.S. PATENT DOCUMENTS

| | | | |
|---|---|---|---|
| 4,509,360 A | 4/1985 | Erwin et al. | |
| 5,009,102 A | 4/1991 | Afromowitz | |
| 5,433,112 A | 7/1995 | Piche et al. | |
| 5,951,163 A | 9/1999 | Jen et al. | |
| 7,824,164 B2 * | 11/2010 | Hakoda et al. | ................ 425/145 |
| 2002/0038160 A1 | 3/2002 | Maynard | |

FOREIGN PATENT DOCUMENTS

| | | |
|---|---|---|
| DE | 199 44 709 A1 | 4/2000 |
| FR | 2 012 207 | 1/2010 |
| GR | 1 346 095 | 2/1974 |
| JP | 53-130764 A | 11/1978 |
| JP | 1-195013 A | 8/1989 |
| WO | 01/96854 A3 | 12/2001 |

OTHER PUBLICATIONS

"Ultrasonic investigations of the thermoplastics injection moulding process" by W. Michaeli, C. Starke, Polymer Testing, pp. 205-209.
Abstract for "Ultrasonic Measurements on Thermoset Moulding Compounds"—article in German language is attached.

* cited by examiner

*Primary Examiner* — Timothy Heitbrink
(74) *Attorney, Agent, or Firm* — Vidas, Arrett & Steinkraus, P.A.

(57) ABSTRACT

An apparatus for the measurement of the temperature of a plastified plastic material at the exit of an extruder, characterised in that the function of the sound, velocity in dependence of the temperature is measured and memorised for at least one plastified plastic material, the sound velocity is measured during the extrusion of the plastic material, and the respective temperature is determined from the velocity measurement values and the function.

6 Claims, 2 Drawing Sheets

APPARATUS FOR THE MEASUREMENT OF THE TEMPERATURE OF A PLASTIFIED PLASTIC MATERIAL AT THE EXIT OF AN EXTRUDER

CROSS-REFERENCE TO RELATED APPLICATIONS

Not applicable.

STATEMENT REGARDING FEDERALLY SPONSORED RESEARCH

Not applicable.

BACKGROUND OF THE INVENTION

When cables or the like are sheathed with a plastic material, extruders are used, which plastify the plastic material and inject it round about a core (conductor). The plastic material is made soft by pressure and heat in the extruder, so that it can be applied to the core without problems and without inclusions. For this purpose, it is desired to determine the temperature in the plastified material, in order to achieve an optimum viscosity of the melt for the extrusion process. Furthermore, burning or premature crosslinking in the extruder head must be avoided. Instead, the crosslinking process has to take place immediately after the extrusion. Thus, a reliable temperature measurement optimises the production process.

In such extrusion processes, it is known to measure the temperature of the material at different delivery speeds outside of the extruder head with the aid of a thermocouple. This measurement takes place at a delimited location, and of course it has a relatively long response time. The thermocouple measures only the temperature in the outer region of the melt. If however the thermocouple projects into the melt, the determination of the temperature is distorted by sliding friction effects. Besides to that, the thermocouple negatively affects the flow properties of the melt.

It is also known to measure the temperature of the melt with the aid of an infrared thermometer. However, by doing so, the surface temperature of the melt can be acquired only up to a depth of a few millimeters. When there are special fillers in the melt, the measurement depth is reduced even further.

However, a capture of the mass temperature of plastics melts that is as accurate as possible can help to increase the production output of an extrusion plant significantly, namely in that amongst others the idle time (for instance cleaning of the plant, repair etc.) of the plant is reduced by selecting an optimum temperature.

Thus, the present invention is based on the objective to indicate a method for the measurement of the temperature of at least one plastified plastic material at the exit of an extruder, which permits an accurate non-contact, non-invasive temperature measurement of a melt in a simpler way.

BRIEF SUMMARY OF THE INVENTION

In the method of the present invention, the function of the sound velocity in dependence of the temperature is measured and memorised for at least one plastified plastic material. During the extrusion of the plastic material, the sound velocity is measured in the extruder, preferably transversely to the flow direction of the plastic material, and the respective temperature is determined from the velocity measurement values and the memorised function.

The present invention starts from the finding that the sound velocity in plastics melts, in polyethylene melts in particular, exhibits a strong temperature dependence. Using this dependence, the mean temperature of the plastics melt can be determined across a pipe cross section by determining the mean sound velocity.

The ultrasound sensors used in this do not need any contact with the plastics melt, and thus they permit a non-contact, non-invasive determination of the mean sound velocity, and by this of the mean mass temperature of the melt.

The temperature determination according to the present invention can be performed in real time, is accurate and does not impair the melt. As the sound velocity is measured transversely across the melt, it is possible to determine the mean mass temperature of the melt accurately in this way.

An additional thermocouple projects directly up to the melt, and so it measures the surface temperature of the melt in the edge region of the pipe cross section. When the flow profile of the melt is known, conclusions about the distribution of the temperature within the pipe cross section can be drawn from the surface temperature and the mean mass temperature.

The sound velocity in the melt depends also of the pressure in a certain degree, so that a pressure compensation should occur. According to the present invention, the function of the sound velocity in dependence of the pressure is measured for at least one plastified plastic material for this purpose. The function is memorised, and a pressure measurement takes place during the extrusion, besides to the sound velocity measurement. Even in this, it is of course proceeded in a non-invasive manner. A pressure-compensated temperature of the melt is then determined from the measurement values and the memorised functions of sound velocity and pressure.

Before an extruder can start with the production, it is of course necessary to melt the starting material sufficiently, so that it leaves the extruder head as a homogeneous extrudate. As is well known, this takes place by heating the material in the extruder, a further warming-up through friction taking place in this during the advancing in the extruder with the aid of an extruder screw. By determining the temperature of the plastics melt and producing extruded samples at certain time intervals, the machine operator determines when the production of an extrudate can be started. A prerequisite is that the material is completely molten and there are no more islands of not molten materials therein, which would impair the quality of the produced material. Consequently, the machine operator observes the material that was extruded as a sample at first, and decides based on her/his experience when the production can be started.

For reasons of the optimisation of the production output, one desires to keep the temperature of the plastics melt in the extruder as high as possible, namely shortly below that temperature at which burning or carbonization of the material might occur. Upon longer operation of an extruder in particular, it may happen that particles of crosslinked or burned material are formed by which the produced extrudate becomes defective. Such particles can impair the breakdown resistance in high voltage cables. In water- or gas pipes, the tightness of the pipe wall can be impaired.

Therefore, the present invention is based on the further objective to provide a method for the operation of an extruder for extruding a plastic material in order to form an extrudate of plastic material in which the production of the extruder is controlled more accurately and the formation of extrusion products that are free of defects is ensured.

In the method according to claim 4, the propagation velocity of sound waves that are sent transversely to the flow direction of the flowable material is measured closely to or on the head of the extruder in short time distances or continuously during the initial extrusion. A plastics extrudate is produced only then when the course of the measurement values has a substantially steady tendency or is substantially constant.

The present invention starts from the finding that the propagation velocity of sound waves in the material that is to be extruded does not only depend on the temperature thereof, but also from the condition in which the same is. The propagation velocity in the solely liquid condition of the plastics material is measurably smaller than that in the material which is in the solid or only incompletely plastified condition. Therefore, if there are particles or islands of not already molten material in the melt when the extruder operation is started, this becomes noticeable through fluctuations of the measurement values for the propagation velocity of the sound waves. Namely, if the plastics material would uniformly pass over into melt in the gradual temperature increase, the temperature would rise gradually, and the sound velocity would fall off gradually. The measurement values would have a steady tendency. However, if solid particles or islands migrate through the measurement region, measurable fluctuations of the propagation velocity occur. From this it is recognised that the melt in or on the extruder head has not yet the sufficient homogeneity for beginning the production. The other way, the production can be started as soon as the course of the measurement values has a steady tendency, for instance when it is slightly dropping or constant. Thus, by the method of the present invention the machine operator is given a means at hand to determine the point in time of production by way of the extruder at such a point in time where products free of defects can be produced as soon as possible, without that unusable material would be unnecessarily turned out. According to experience, the same is later recycled and is not lost, but it cannot be used for the intended production for the time being.

The course of the measurement values can be displayed by suitable means.

In the method according to claim 5, the propagation velocity of sound waves is measured continuously or in short time distances during the production of the plastics extrudate. The production is stopped when the fluctuation range of the measurement values exceeds a given value. Even in this method, the finding is used that particles or solid constituents in a melt influence the propagation velocity of sound waves. As was already set forth, local burning and carbonizations of the plastic material due to local overheating can occur during the production. If the same are incorporated into the extruded product, it becomes defective. This may be of little importance for relatively simple extrudate-formed plastics products. But for the production of high voltage cables, of gas or water pipes and the like, such defects cannot be tolerated. With the aid of the method of the present invention, it is possible to recognise these defects instantly and to stop the production process in order to maintain the desired quality of the extruded products.

As already set forth, the propagation velocity of sound waves in a plastics melt permits conclusions about the temperature thereof, if it is known how the sound propagation velocity in dependence of the temperature behaves for special plastics. This can be easily determined by previous measurements. The methods according to the present invention described at last can be linked with the temperature measurement, so that not the course of the sound propagation values is evaluated, but instead the course of the temperature values.

A device for performing the method of the present invention provides a tubular adapter piece at the exit of the extruder, on which an ultrasound sender and diametrically to it an ultrasound receiver are radially arranged. The sensors are preferably arranged in a radial recess in the wall of the adapter piece. If the adapter piece has a wall thickness of 10 mm for instance, a remaining wall thickness of for instance only 1 mm remains due to the recess. Because the propagation velocity of sound in steel is almost four times that in the plastics melt, the corruption of the measured sound velocity by the remaining wall thickness of the recess plays a minor role. Besides to this, it is of course possible to correct this error. In order to minimise possible reflections and diffractions at unevennesses, one embodiment of the present invention provides that the contact surface in the bottom of the recess is polished.

BRIEF DESCRIPTION OF THE SEVERAL VIEWS OF THE DRAWINGS

The present invention will be explained in more detail below by means of drawings.

DETAILED DESCRIPTION OF THE INVENTION

Figure 1:
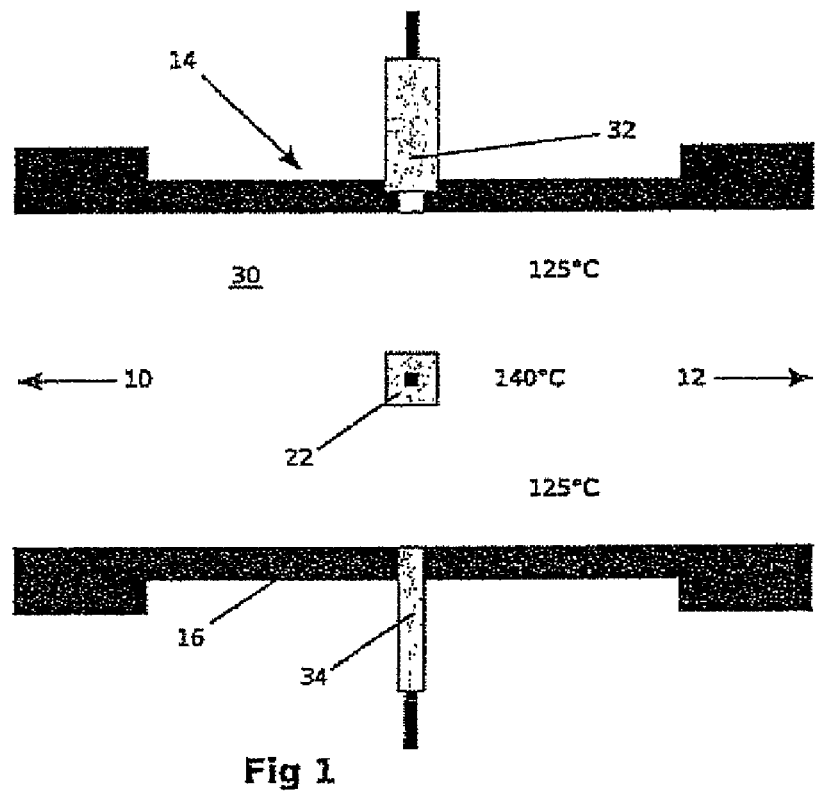
FIG. 1 shows an adapter piece according to the present invention.
Figure 2:
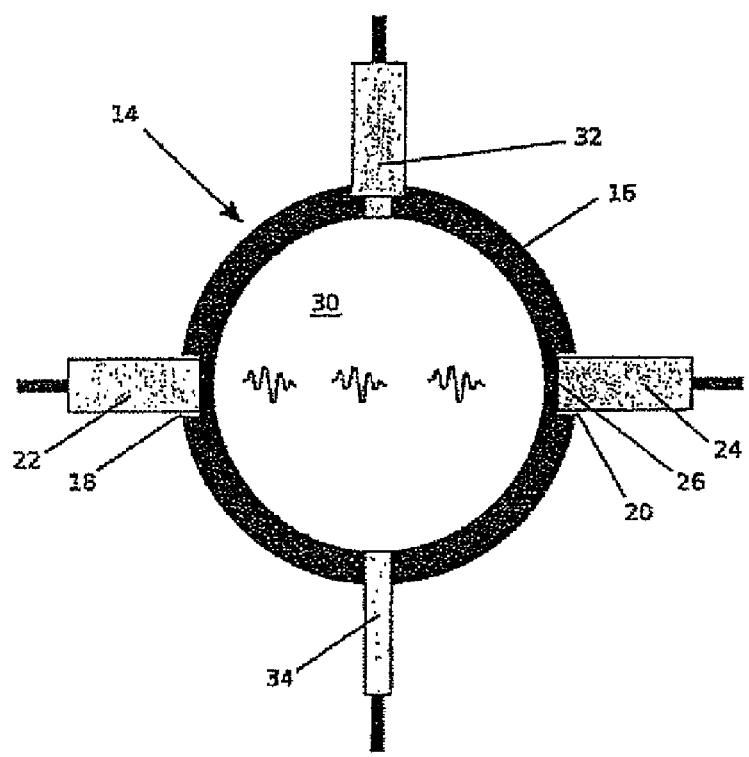
FIG. 2 shows a section through the adapter piece according to FIG. 1.
Figure 3:
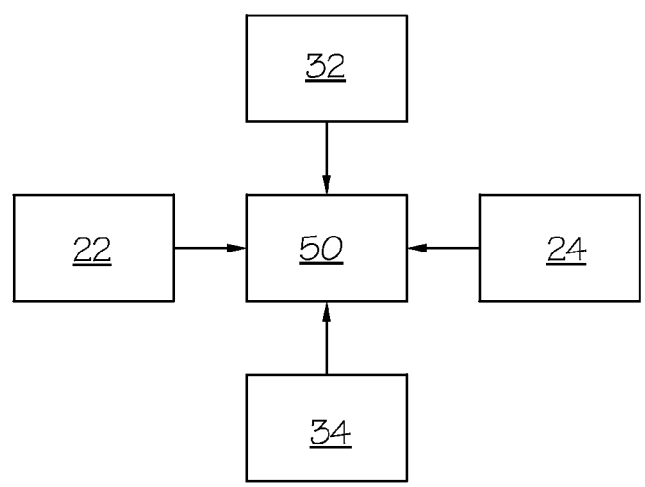
FIG. 3 shows a schematic view of the measuring device 50.

While this invention may be embodied in many different forms, there are described in detail herein a specific preferred embodiment of the invention. This description is an exemplification of the principles of the invention and is not intended to limit the invention to the particular embodiment illustrated A tubular adapter piece 14 is arranged between the front end of an extruder 10 and the extruder head 12. The extruder and also the fixation of the adapter piece will not be described in detail. The fixation of the adapter piece can be made in a simple way by known means. The extrusion temperature for polyethylene is to be designated by the indicated temperature values of 125° C. and 140° C., respectively. LDPE varies in its temperature between 100° C. and 200° C.

The adapter piece 14 has a cylindrical wall 16, with a thickness of for example 10 mm. Diametrically opposite recesses 18 and 20, respectively, are machined from the exterior into the cylindrical wall 16, into which probes 22 and 24, respectively, are set in. The probe 22 contains an ultrasound sender and the probe 24 an ultrasound receiver. The recesses spare out a remaining wall thickness 26 of for instance 1-2 mm. The bottom of the recesses 18, 20 is polished, so that no reflections and unnecessary diffractions of the sound signal can take place. With the aid of the ultrasound sender and -receiver, the sound velocity in a plastics melt 30 is measured within the adapter piece 14. For instance, the sound velocity of the polyethylene melt is 1500 m/s. The sound velocity in steel, from which the adapter piece 14 is made, is about 5900 m/s. Therefore, the measurement of the sound velocity yields a certain error that is provoked by the remaining wall thickness 26. However, this plays a minor role in the measurement of the mean sound velocity of the melt, and if necessary it can be corrected.

Before a temperature measurement of the plastics melt, the dependence of the sound velocity from the temperature of the plastics is determined for the respective plastic material, which will mostly be linear in the relevant temperature range. This function is memorised in an analysing device. By measuring the respective sound velocity, the respective temperature can therefore be determined from the function. The temperature measurement takes place in real time, and therefore measures can be initiated immediately, in order to effect a temperature change in case that the measured temperature deviates from a given value.

The sound velocity on its part depends of the pressure in the melt. In order to permit a temperature measurement with the aid of the measured function, the pressure in the melt should be also taken into account. A pressure sensor 32 is associated to the adapter piece 14 for this purpose.

The surface temperature of the melt 30 can also be determined with the aid of a thermocouple 34, which is arranged in the wall 16 diametrically opposite to the pressure sensor 32, in order to be able to draw conclusions regarding the temperature distribution within the pipe cross section when the flow profile and the mean mass temperature of the melt are known.

The measurement of the propagation velocity of sound or through this also of the temperature of the melt, respectively, can not only be used in order to produce as near as possible to the upper still admissible temperature limit in order to keep the output at maximum, but even in order to control the beginning of an extrusion or to stop an error-impaired production. A production should begin only when the plastics melt in or on the extruder head, respectively, is homogeneous in a high degree. As an inhomogeneous plastics melt results in another propagation velocity of the sound than a homogeneous one, the selected temperature course of the melt is an indication whether homogeneity has been achieved. Before this, solid particles present in the melt would cause temperature fluctuations, which should normally not occur. As soon as the temperature course has a steady tendency, the machine operator can allow the extruder to produce. This method has the advantage that the machine operator must no more take samples, but has only to wait until the material in or on the extruder head is completely molten.

If there are fluctuations of the temperature course during a production, which cannot occur due to other reasons, this is a sign for an inhomogeneity of the material, due to burning products in particular. The machine operator can therefore stop the extruder when this occurs, and by doing so he/she can prevent the production of defective products. It is to be understood that stopping the extruder or ending the production can take place also automatically, in that an analysing device detects the fluctuation range of the temperature measurement values and provides a stopping signal when the latter exceeds a given value.

What is claimed is:

1. A device for the measurement of the temperature of a plastified plastic material at the exit of an extruder, comprising:
   a tubular adapter piece (14) is arranged at the exit of an extruder, on which an ultrasound sender (22) and diametrically to it an ultrasound receiver (24) are radially arranged, a pressure sensor (32) is arranged in the wall (16) and
   an analyzing device is operatively connected to the ultrasound sender and ultrasound receiver, and the analyzing device is constructed and arranged to measure and record the sound velocity in dependence of the temperature for at least one plastified plastic material, the sound velocity being measured during the extrusion of the plastic material, and the respective temperature being determined from the velocity measurement values and a substantially linear function relating the velocity and temperature in the plastic material, wherein the analyzing device is further constructed and arranged to measure the sound velocity of the plastic material in dependence of the pressure of the plastic material, and further measure a pressure value of the plastic material during the extrusion of the plastic material, and perform a pressure compensation of the temperature measurement with the aid of the pressure measurement value.

2. A device according to claim 1, characterised in that sender and receiver for ultrasound (22, 24) are arranged in radial recesses (18, 20) in the wall (16) of the adapter piece (14).

3. A device according to claim 2, characterised in that the remaining wall thickness of the pipe wall is minimized with the aid of the recess (18, 20) such that only a small part of the pipe wall of the adapter oscillates, in order to decrease the blur of the signal in the region of the ultrasound coupling.

4. A device according to claim 2, characterised in that with the aid of the recess (18, 20), the remaining wall thickness is minimized such with respect to the pipe wall that a lateral signal propagation into the pipe wall is suppressed in a high degree, and a good signal distribution is achieved in the irradiation direction of the ultrasound sender.

5. A device according to claim 2, characterised in that the bottom of the recess (18, 20) is polished in order to minimize reflections and diffractions of the ultrasound signal on the contact surface.

6. A device according to claim 1, characterised in that a thermocouple for measuring the surface temperature of the melt is arranged in the wall (16) of the adapter piece (14).

\* \* \* \* \*